(12) United States Patent
Taylor et al.

(10) Patent No.: US 11,484,440 B2
(45) Date of Patent: Nov. 1, 2022

(54) MAGNETORHEOLOGICAL ELASTOMER AND MAGNETORHEOLOGICAL FLUID FOR CLINICAL WRAP

(71) Applicant: Stryker Corporation, Kalamazoo, MI (US)

(72) Inventors: Gregg Taylor, Kalamazoo, MI (US); Alexey Titov, Redmond, WA (US); Hieu Phan, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 556 days.

(21) Appl. No.: 16/389,154

(22) Filed: Apr. 19, 2019

(65) Prior Publication Data

US 2019/0321217 A1     Oct. 24, 2019

Related U.S. Application Data

(60) Provisional application No. 62/660,560, filed on Apr. 20, 2018.

(51) Int. Cl.
*A61F 7/02*     (2006.01)
*C08K 3/08*     (2006.01)
(Continued)

(52) U.S. Cl.
CPC .................. *A61F 7/02* (2013.01); *C08K 3/08* (2013.01); *A47G 9/0215* (2013.01); *A47G 2009/004* (2013.01); *A47G 2009/008* (2013.01); *A61F 2007/0022* (2013.01); *A61F 2007/0029* (2013.01); *A61F 2007/0043* (2013.01); *A61F 2007/0054* (2013.01); *A61M 60/40* (2021.01); *C04B 14/34* (2013.01);
(Continued)

(58) Field of Classification Search
CPC .................. C08K 2201/01; C08K 3/08; A61F 2007/0054; A61F 2007/0246; A61F 7/02; A47G 9/0215; A47G 2009/004; A47G 2009/008; C08L 2203/02; A61G 7/00; H01F 1/447
See application file for complete search history.

(56) References Cited

U.S. PATENT DOCUMENTS 4,132,262 A * 1/1979 Wibell ................. A47G 9/0215
                                                                                   165/206
4,596,250 A    6/1986 Beisang, III et al.
(Continued)

FOREIGN PATENT DOCUMENTS

WO    WO-2014209295 A1 * 12/2014 ........... G06F 1/1652

*Primary Examiner* — Linda C Dvorak
*Assistant Examiner* — Lindsay Regan Lancaster
(74) *Attorney, Agent, or Firm* — Howard & Howard Attorneys PLC

(57) ABSTRACT

A reinforcing clinical wrap is provided with integral thermal management. The clinical wrap includes a fluid circuit for a heat transfer medium to circulate between a fluid inlet and a fluid outlet. A shape conforming medium is disposed within a portion of the clinical wrap providing selective reinforcement support of the portion of the clinical wrap to conform to a surface of a patient. Non-limiting examples of the shape conforming medium may include a magnetorheological elastomer, a magnetorheological elastomer, a magnetorheological foam, a UV curable resin, and a phase change material.

13 Claims, 5 Drawing Sheets

(51) Int. Cl.
  *C08L 57/00*  (2006.01)
  *A61F 7/00*  (2006.01)
  *A47G 9/00*  (2006.01)
  *A47G 9/02*  (2006.01)
  *C04B 14/34*  (2006.01)
  *A61M 60/40*  (2021.01)

(52) U.S. Cl.
  CPC ............ *C08K 2003/0843* (2013.01); *C08K 2003/0856* (2013.01); *C08K 2003/0862* (2013.01); *C08K 2201/01* (2013.01); *C08L 57/00* (2013.01); *C08L 2203/02* (2013.01)

(56) References Cited

U.S. PATENT DOCUMENTS

| | | |
|---|---|---|
| 6,755,852 B2 | 6/2004 | Lachenbruch et al. |
| 6,859,967 B2 * | 3/2005 | Harrison ............... A61G 7/001 |
| | | 5/710 |
| 2007/0073368 A1 | 3/2007 | Cazzini et al. |
| 2014/0276257 A1 * | 9/2014 | Santa Maria ........... A61H 9/00 |
| | | 601/18 |
| 2016/0008159 A1 * | 1/2016 | Mazzucchelli ......... A61F 5/058 |
| | | 602/6 |
| 2016/0346115 A1 | 12/2016 | Varga et al. |

\* cited by examiner

MAGNETORHEOLOGICAL ELASTOMER AND MAGNETORHEOLOGICAL FLUID FOR CLINICAL WRAP

CROSS REFERENCE TO RELATED APPLICATIONS

This application claims the benefit of U.S. Provisional Application No. 62/660,560, filed on Apr. 20, 2018, which is incorporated herein by reference in its entirety.

BACKGROUND

Clinical wraps, or patient wraps, are used to provide various treatments for wounds of a patient, and can be of various sizes and shapes. In certain aspects, clinical wraps may be useful with various compression therapies, the treatment of ulcers, and the like. In other aspects, clinical wraps may additionally or alternatively be used to assist in immobilizing limbs or specific body regions of a patient. For example, when transporting a patient, it is advantageous to keep a patient stable and immobile to reduce the risk of further injuries.

Another consideration is regulating patients' body temperature while using clinical wraps or patient wraps. Various external temperature transfer devices (TTDs) may be used to provide thermal conduction/convection to warm or cool a patient. In order to maximize the thermal conduction/convection, the TTD should have a proper interface with the patient to allow the appropriate heat transfer to occur. For example, a TTD that does not conform to a body contour of a patient, or that otherwise leaves an air gap or other interruption between the TTD and the patient, will most likely decrease the level thermal transfer that can take place via conduction/convection. Conventional clinical wraps used as immobilizing devices may not be capable of being used in conjunction with TTDs, and vice versa.

BRIEF DESCRIPTION OF THE DRAWINGS

The present teachings will become more fully understood from the detailed description and the accompanying drawings, wherein.

Figure 1:
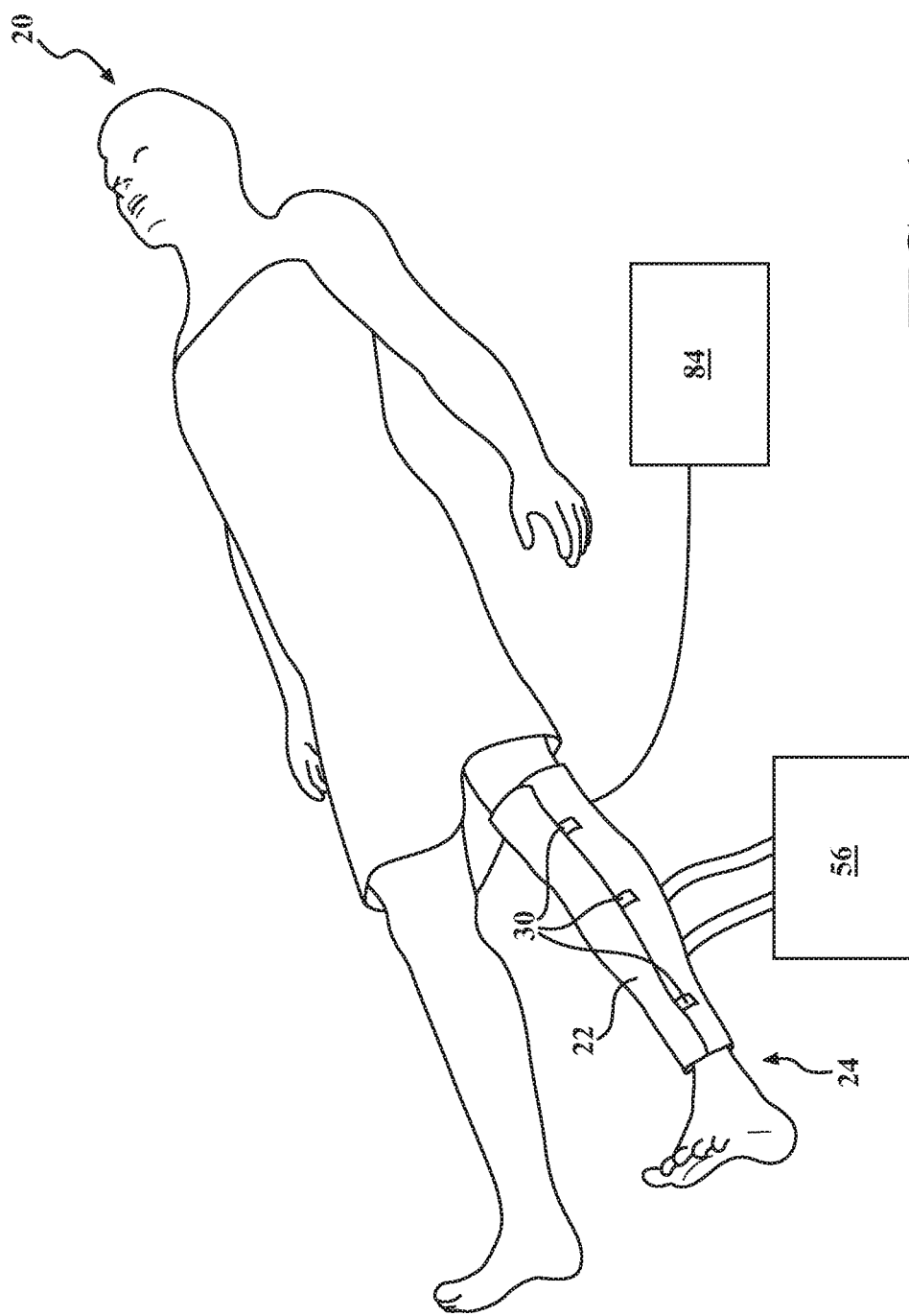
FIG. 1 is an isometric view of a patient with an exemplary clinical wrap contoured about a leg of the patient.

It should be noted that the figures set forth herein are intended to exemplify the general characteristics of the systems, methods, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures, while other aspects may incorporate only portions of features from a single figure.

DETAILED DESCRIPTION

The present technology generally provides an enhanced clinical wrap, also known as a patient wrap, with both reinforcement and compressive features to assist with immobility, as well as integral thermal management features. In various aspects, a clinical wrap in accordance with the teachings of present technology may generally be provided having two functional materials contained therein: a shape conforming material, and a heat transfer medium. In this regard, the present technology provides a close conforming clinical wrap that can be used to selectively immobilize a limb or specific body region of a patient, while also assisting in maintaining an appropriate body temperature of the patient. As detailed herein, this can be accomplished by providing a clinical wrap conformed to a shape and contours of a patient, preferably without interruptions such as air gaps between the wrap and the patient. Once properly conformed, the clinical wrap is provided with a certain degree of rigidity upon selective actuation of the shape conforming material. At the same time, the heat transfer medium of the clinical wrap is configured to adjust and/or maintain a temperature of the clinical wrap, or a designated region or portion thereof, that interfaces with or is in contact with a surface of the patient during use. The clinical wraps of the present technology can be used for short durations, for example, during the transfer of a patient, as well as for longer durations, such as in a medical or care facility, when it is desirable to keep a patient stable and immobile.

In one aspect, the shape conforming material can be a shape conforming medium such as a fluid or a deformable solid that may have a flexible matrix or some degree of flexibility. Non-limiting, exemplary shape conforming mediums, as provided in more detail below, may include magnetorheological fluids, magnetorheological elastomers, magnetorheological foams, UV curable resins, and phase change materials. Where the shape conforming medium is a fluid, it may be configured to selectively change state between a relatively low viscous state and a more rigid, or relatively high viscous state leading to an increased rigidity, suitable for immobilizing a limb or body region of a patient. Where the shape conforming medium is a deformable solid, such as an elastomer or resin, it may be configured to selectively change state between a generally soft and elastic polymer or flexible film, and a more rigid, relatively stiff matrix. As discussed in more detail below, in various aspects, the change in viscosity and/or rigidity may be reversible and the clinical wrap can be repositioned and used multiple times. This will allow for a caregiver or medical professional to temporarily deactivate the clinical wrap such that is becomes flexible for easy removal or adjustments, especially when certain wounds or treatments require regular check-ups and viewing. Reactivation of the clinical wrap preferably provides a consistency in the amount of rigidity and pressure applied to the patient, even when operated by different users. In other aspects, the change in state of the shape conforming material may be irreversible, and the clinical wrap is provided as a single use device.

The heat transfer medium can be a heat transfer fluid, such as water, oil, or a non-toxic liquid, configured to circulate through at least a portion of the clinical wrap at a specific temperature. In other aspects, the heat transfer medium can be a gas flowing through at least a portion of the clinical wrap. In the various different aspects, the heat transfer medium serves to alter or maintain a temperature of a surface adjacent to, or an interface in direct contact with, the patient, such as the patient's skin.

For a more complete understanding of the present teachings, reference is made to FIG. 1, which is an isometric view of a patient 20 with an exemplary clinical wrap 22 contoured about the shape of a limb 24 of the patient 20. As shown in FIG. 1, the clinical wrap 22 is specifically wrapped around and conforming to a lower medial limb 24. For best results and optimal heat transfer, the interior of clinical wrap 22 should be contacting the skin of the patient 20, but it should not be over tight. For example, in various aspects the interior of the clinical wrap 22 may be in direct contact with the patient's skin. In aspects where there may be a bandage or other medical treatment material in touch with the patient, the interior of the clinical wrap should have as close an indirect contact with the patient's skin as possible without having an adverse effect with respect to the other medical treatment. This contact between the clinical wrap 22 and the patient 20 will assist in providing efficient thermal conduction/convection using the heat transfer medium. Subsequent activation of the shape conforming medium may slightly increase a pressure applied to the area of patient 20 being treated, however, circulation of the heat transfer medium preferably does not affect the pressure.

It should be understood that clinical wraps 22 made in accordance with the present teachings may be of various shapes and sizes. In certain aspects, the clinical wrap 22 may be custom shaped for a specific limb, appendage, extremity, or portion thereof, while in other aspects, the clinical wrap 22 may be generically provided in different appropriate sizes and shapes for multiple different uses.

The clinical wrap 22 may be configured as a wearable device, such as a vest, neck brace, head wrap, full or partial body wrap, or a tubular shape to be worn by the patient. In other aspects, the clinical wrap 22 may be a substantially planar device that can easily be manipulated in a manner such that it can be conformed to a shape and specific contours of the individual patient. By way of example, certain clinical wraps 22 may be appropriately shaped and sized for different areas of the human body, such as for: upper/lower legs, knees, ankles, and/or feet; upper/lower arms, elbows, wrists, and/or hands; head, neck, and shoulders; upper and lower abdomen or torso; chest area; and combinations thereof.

In still other aspects, a combination of clinical wraps 22 of different sizes may be provided as a kit for a medical professional to subsequently choose a size, shape, type, and number of wraps as appropriate for a given condition or treatment. For example, certain kits may be provided with clinical wraps 22 for one particular body area or region in a number of different sizes, such as small, medium, large, x-large, etc. Other kits may be provided with a combination of different shapes or with clinical wraps 22 for a number of different body areas or regions. For example, the kit may include a collection of various wraps for the neck, chest, and/or limbs in a single size. Custom kits may also be provided, as desired. The clinical wraps 22 may be used individually, or two or more clinical wraps 22 may be used together. For example, two or more clinical wraps 22 may be secured, coupled, or otherwise removably fastened to one another. In aspects where the clinical wraps 22 provide fluid communication and/or fluid transfer, as discussed in more detail below, appropriate inlets, outlets, and fluid connections are provided with the clinical wraps 22. Thus, the clinical wraps 22 may be both mechanically fastened to one another, as well as provide fluid communication between one another.

Figure 2:
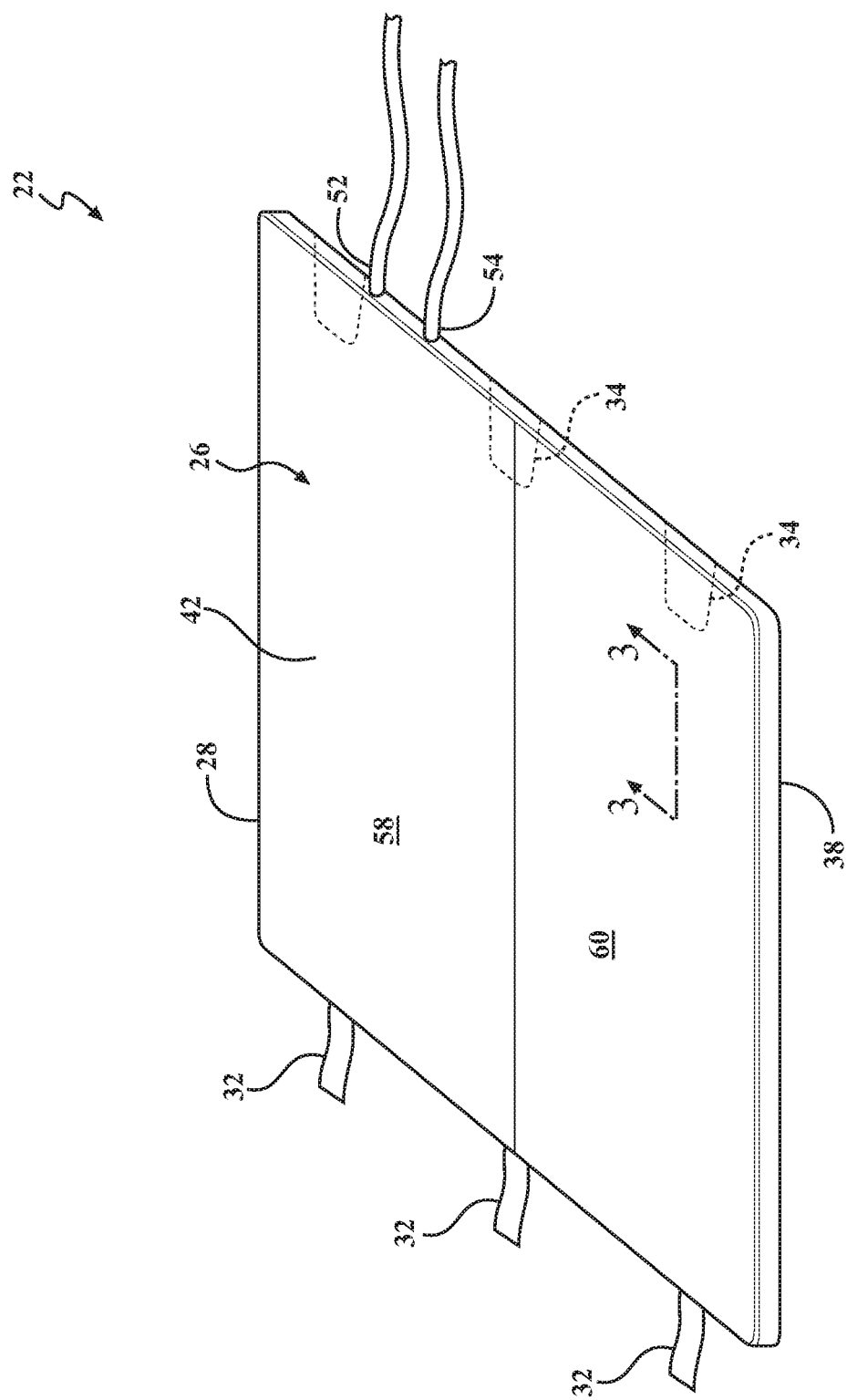
FIG. 2 is an isometric view of an exemplary clinical wrap in a substantially planar arrangement illustrating various details of the clinical wrap according to the present technology.

FIG. 2 is an isometric view of an exemplary clinical wrap 22 in a substantially planar arrangement illustrating various details of the clinical wrap 22. As shown, the clinical wrap 22 is provided with a main body portion 26. While shown with a substantially rectangular perimeter 28 for ease of illustration, it should be understood that the clinical wrap 22 can be provided in various shapes and sizes for its intended purpose. With reference to both FIGS. 1-2, the clinical wrap 22 may be provided with various fastening mechanisms 30 for securing the clinical wrap 22 to the patient. In one example, respective hook and loop straps 32 and pads 34 may be used to couple opposing sides of the clinical wrap 22 together once wrapped and contoured around a limb 24 of the patient 20. Other mechanical fasteners, straps, buttons, and closures can be used as desired, and may be useful to assist in achieving a proper fit for various sized patient appendages, limbs, extremities, etc. Although not shown, the clinical wrap 22 may be provided with one or more apertures of strategic sizes and shapes, and at strategic locations for unobstructed access to certain areas of the patient 20. In other aspects, apertures may provide for the passage of an appendage or extremity of a patient there through.

Figure 3A:
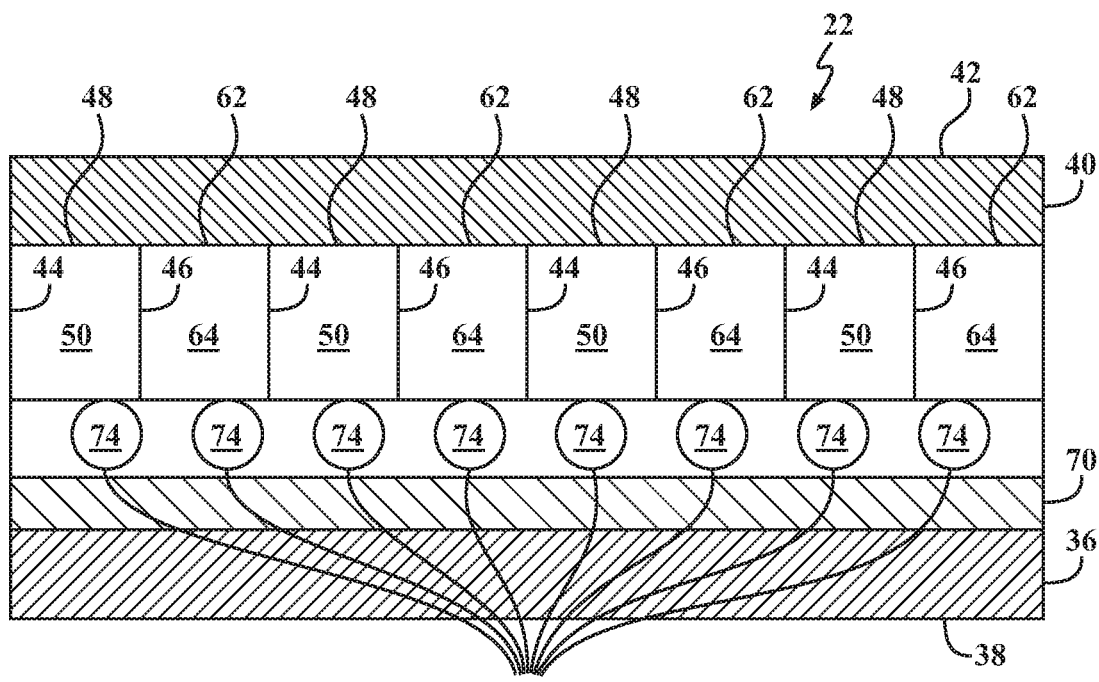
FIG. 3A is a partial cross-sectional view of a portion of the clinical wrap of FIG. 2 taken along the line 3-3 according to a first exemplary aspect, illustrating a number of channels arranged in an alternating side-by-side alignment.
Figure 3B:
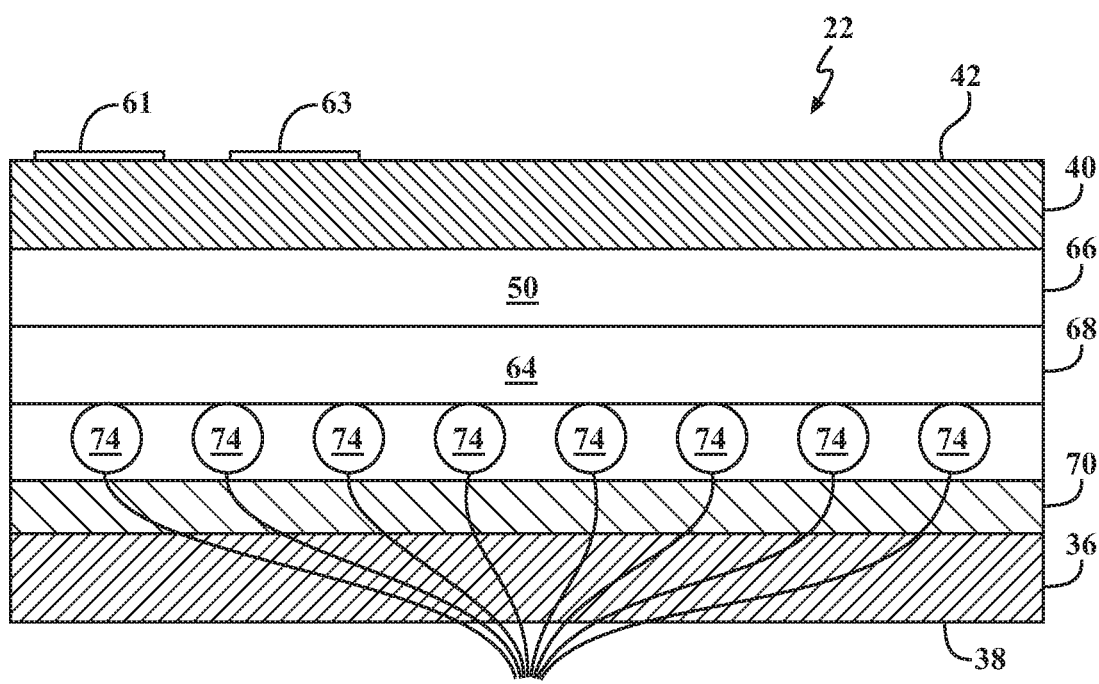
FIG. 3B is a partial cross-sectional view of a portion of the clinical wrap of FIG. 2 taken along the line 3-3 according to a second exemplary aspect, illustrating two fluid reservoirs arranged in an upper and lower respective alignment.
Figure 3C:
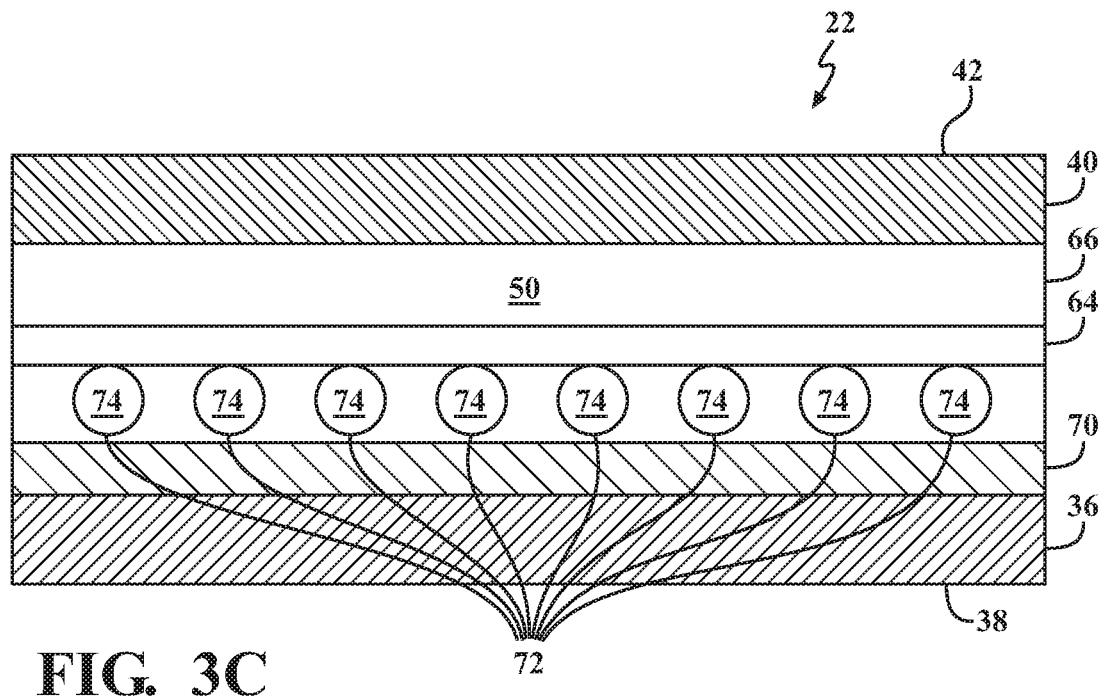
FIG. 3C is a partial cross-sectional view of a portion of the clinical wrap of FIG. 2 taken along the line 3-3 according to a third exemplary aspect, illustrating the shape conforming material as a layer.
Figure 3D:
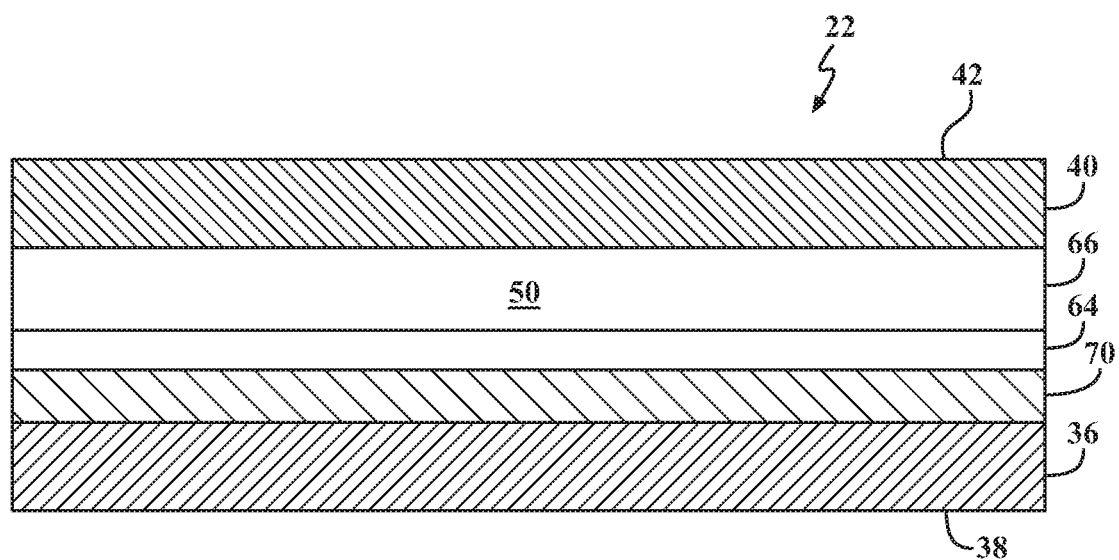
FIG. 3D is a partial cross-sectional view of a portion of the clinical wrap of FIG. 2 taken along the line 3-3 according to a fourth exemplary aspect, illustrating the shape conforming material as a layer.

FIGS. 3A-3D illustrate various aspects of the clinical wrap 22. FIGS. 3A and 3B provide exemplary arrangements with the use of a fluidic shape conforming medium such as a magnetorheological fluid. FIGS. 3C and 3D provide exemplary arrangements with the use of a shape conforming medium provided as a deformable solid that may have a flexible matrix or some degree of flexibility.

FIG. 3A is a partial cross-sectional view of a portion of the clinical wrap 22 of FIG. 2 taken along the line 3-3 according to a first exemplary aspect of the present teachings. As shown, the clinical wrap 22 may include an outermost layer 36 defining an outer major surface 38, configured to be a protective surface, and an innermost layer 40 defining an inner major surface 42, opposite the outer major surface 38, and configured to interface with a surface of the patient 20. While shown as a single layer for simplicity, it should be understood that either or both of the outermost layer 36 and the innermost layer 40 may include multiple layers or include a multi-layered material. The materials used for the outermost layer 36 and the innermost layer 40 can be selected to complement and/or assist with one of the clinical wrap's 22 purpose of conforming to the patient's skin and to optimize heat transfer. The outermost layer 36 may be a woven material, a flexible fabric, a resilient polymer, a silicone, a viscoelastic memory foam or shape retaining material, a plastic, or other suitable material that may be easily cleaned and sterilized and for preventing exposure of the remaining interior of the wrap to an external environment. The innermost layer 40 may similarly be a woven material, a flexible fabric, a resilient polymer, a silicone, a viscoelastic memory foam or shape retaining material, a plastic, or other suitable material that may be easily cleaned and sterilized. The innermost layer 40 and innermost surface 42 are preferably a material suitable for having extended periods of direct contact with the skin of the patient. In certain uses, the clinical wrap 22 may need to be removed or loosened on a regular basis for inspection purposes, and the interior, or innermost surface 42, should preferably exhibit non-adhesive qualities. As discussed above, for certain wound treatments and use of the clinical wrap 22, the innermost surface 42 may be in direct contact with the skin of the patient 20. For other treatments, there may be indirect contact of the innermost surface 42 with the patient 20, for example, where there may be an intermediate medicated layer, liner, or the like present for a particular treatment.

FIG. 3A illustrates first and seconds sets of adjacent channels 44, 46 arranged in an alternating side-by-side alignment with one another. While shown directly adjacent one another, the channels 44, 46 may also be provided separated or spaced a small distance apart from one another. The walls of the channels 44, 46 are preferably flexible in order to allow the clinical wrap 22 to be shaped and conformed to the patient 20 prior to activation of the shape conforming medium. In various aspects, an exemplary clinical wrap 22 may be provided with a first set of channels 44 that collectively defines a first fluid circuit 48 for a heat transfer medium 50 to circulate throughout the clinical wrap 22, generally between a fluid inlet 52 and a fluid outlet 54 defined in or otherwise coupled with the clinical wrap 22.

In certain aspects, with renewed reference to FIGS. 1-2, the fluid inlet 52 and fluid outlet 54 may be coupled to an external heat exchanger device 56, such as a portable heating and/or cooling unit. In this regard, the clinical wrap 22 may also be provided with a number of different zones 58, 60 that can be provided with different thermal operating parameters. For simplicity, only two zones 58, 60 are shown in the illustration. However, it should be understood that the number, sizes, locations, and shapes of the zones may vary based on the desired end use.

In certain aspects, each zone 58, 60 may be provided with separate fluid inlets 52 and fluid outlets 54, and may be configured for maintaining a different temperature in each zone 58, 60. In this regard, one or more temperature sensor 61 (shown in FIG. 3B) may be strategically provided at various locations of the clinical wrap 22 in order to monitor a temperature of the patient, a temperature of a particular zone, a temperature of the heat transfer medium passing at a specific location, or a combination thereof. Similarly, it may be also desirable in certain aspects that the zones 58, 60 be maintained with different pressures exerted between the clinical wrap 22 and the patient 20. Thus, one or more pressure sensor 63 (shown in FIG. 3B) may be strategically provided at various locations of the clinical wrap 22 in order to monitor a respective pressure exerted against the patient 20 at a particular zone or at one or more strategic location within the clinical wrap 22 to monitor the selective activation of the shape conforming medium 64. While the temperature sensor 61 and pressure sensor 63 are shown in FIG. 3B as being coupled to the innermost surface 42 of the clinical wrap for simplicity of illustration, the sensors may be placed at various other locations for appropriate temperature and pressure readings.

The second set of channels 46 as provided in FIG. 3A collectively defines a second fluid circuit 62, providing fluid communication for a fluidic shape conforming medium 64 through a portion of the clinical wrap 22 that is designed or otherwise configured to interface with a patient and benefit from the immobilizing features provided by the selective activation of the shape conforming medium 64. In various aspects, the second fluid circuit 62 is a closed circuit, although it is also contemplated that in certain aspects it may be desired that the second fluid circuit 62 optionally be provided with a respective fluid inlet and/or fluid outlet if it is required to change, replace, or otherwise access the shape conforming medium 64.

FIG. 3B is a partial cross-sectional view of a portion of the clinical wrap 22 of FIG. 2 taken along the line 3-3 according to a second, alternative exemplary aspect of the present teachings. Differing from FIG. 3A, the channels of FIG. 3B are arranged in what is referred to herein as a fluid pad arrangement, where the channels are instead defined as larger reservoirs 66, 68, as shown in a respective upper and lower alignment with one another. For example, a first reservoir 66 may be defined to store and transfer the heat transfer medium 50 through a portion of the clinical wrap 22 that is designed or otherwise configured to directly or indirectly interface with a patient, and ultimately provide fluid communication between the fluid inlet 52 and a fluid outlet 54 defined in, or otherwise coupled with, the clinical wrap 22. A second reservoir 68 may be present to contain the shape conforming medium 64, and optionally providing fluid communication for the shape conforming medium 64 to move through the clinical wrap 22, with an optional inlet and outlet as described with respect to FIG. 3A.

It should be understood that while FIG. 3B illustrates one reservoir 66 for the heat transfer medium, and one reservoir 68 for the shape conforming medium, the clinical wraps 22 may be provided with a number of reservoirs 66, 68, in a number of different zones, with appropriate fluid communication between the respective reservoirs. In other aspects, multiple reservoirs may be provided in a layered arrangement. Similar to the features discussed with FIG. 3A, it may be desirable to provide the clinical wrap 22 of FIG. 3B with different zones coupled to a heat exchanger device 56, operable to be provided with different temperatures, as well as with different pressures exerted against the patient 20.

As shown in FIG. 3B, the first reservoir 66 containing the heat transfer medium 50 is preferably provided adjacent the patient 20 in an assembled state, in order to provide increased thermal conduction/convection between the heat transfer medium 50 and the patient 20. The reverse arrangement may be provided, as desired. In both aspects depicted in FIGS. 3A and 3B, at least one optional thermally insulating layer 70 of known insulating materials may be provided, such as a medical grade foil or heat reflective thin plastic sheeting including biaxially-oriented polyethylene terephthalate, as sold under the trade name Mylar. Preferably the thermally insulating layer 70 is adjacent the outermost layer 36 of the clinical wrap 22 in order to increase the thermal conduction/convection efficiency, and to insulate the clinical wrap 22 from an external environment.

When present as a fluid, the shape conforming medium 64 of the present technology is preferably disposed throughout the second set of channels 46 (FIG. 3A), the second reservoir 68 (FIG. 3B), or a portion thereof, in order to provide a selective "locked in" reinforcement support of at least a portion of the clinical wrap 22, such that it rigidly conforms to an interface with, or surface of, the patient 20. The second set of channels 46 may be patterned and/or shaped to selectively maintain the clinical wrap 22 at a predetermined configuration to essentially immobilize at least a portion of the patient 20 when the shape conforming medium 64 becomes rigid with an increased viscosity. In one aspect of the present technology, the shape conforming medium 64 exhibits a variable viscosity in response to an exposure to a magnetic field. For example, the shape conforming medium

64 may be a non-toxic, viscous carrier, such as an oil, that includes at least one shape changing material, such as a magnetorheological fluid (MRF). An MRF is generally a carrier fluid, such as an oil, that includes ferromagnetic particles randomly distributed therein in a functional suspension under normal circumstances. In one example, the ferromagnetic particles may be present as having a three dimensional shape, such as a sphere, ellipsoid, or the like. The ferromagnetic particles may have symmetrical as well as non-symmetrical or irregular shapes, and may also be present as rod-shaped or elongated particles. The shape conforming medium 64 has the capability of changing one or more of its material properties, preferably viscosity (or the apparent viscosity), through the use of an external stimulant, preferably a magnetic field. For example, when a magnetic field is generated or otherwise applied, the ferromagnetic particles align themselves along the lines of the magnetic field, or magnetic flux.

Exemplary ferromagnetic particles include alloys of iron, nickel, and cobalt. Ceramics, such as sintered compositions of iron oxide and barium/strontium carbonate, as well as rare earth magnets, such as neodymium and samarium-cobalt, may also be useful with the present technology. The maximum possible magnetic field induced change in stress/modulus generally occurs when the aligned particles become magnetically saturated. While iron has been shown to have the highest saturation magnetization of elements, certain iron and cobalt alloys have even higher saturation magnetizations. Iron and cobalt alloys may also be preferred in certain aspects due to their high permeability and relatively low hysteresis loss.

Generally, the ferromagnetic particles may be randomly distributed within the shape conforming medium 64 when no magnetic field is applied. In the presence of a magnetic field of sufficient strength, however, the particles quickly acquire a magnetic polarization and will form chains of various strength, based in part on the strength of the magnetic field. It should also be understood that many of the specific features of the ferromagnetic particles such as their size/shape, distribution in the matrix, and percentage volume of the magnetic particles in the fluid or elastomer matrix can affect the overall behavior of the shape conforming medium 64.

In various aspects, it may be desired to control a buoyancy or relative density of the ferromagnetic particles to minimize particle settling and agglomeration. Thus, the ferromagnetic particles may be provided having different average sizes, weights, and content in order to provide a distribution of ferromagnetic particles with a range of densities to enhance dispersion. For example, certain of the ferromagnetic particles may be provided as solid particles, and other particles may be provided having a shell with a core. The core may be hollow or may be filled with a gas or other material in an effort to adjust density and buoyancy. Particles with different core sizes may be provided as appropriate for variations in density. Certain of the ferromagnetic particles may also be provided with an outer coating, for example, an outermost polymer coating such as silicone or the like. Preferably, a thickness of the polymer coating can be selected providing a sufficient buoyancy control to minimize settling of the particles, yet providing the same functionality to form a rigid shape conforming medium 64 upon being subjected to the magnetic field. In various aspects, the polymer coating itself may also be magnetically conductive. In still other aspects, the rate and degree to which settling and agglomeration occurs may be offset to a degree with the use of a surfactant additive. However, it should be understood that the addition of a surfactant may negatively affect the magnetic saturation of the fluid, which, in turn, may affect the maximum yield stress exhibited in the activated state, which is, in turn, related to the change in apparent viscosity of the shape conforming medium 64.

FIG. 3C is a partial cross-sectional view of a portion of the clinical wrap 22 of FIG. 2 taken along the line 3-3 according to a third, alternative exemplary aspect of the present teachings. Differing from FIGS. 3A-3B, FIG. 3C provides the shape conforming medium 64 as a layer, or sheet, in the clinical wrap 22, without being disposed within a fluid reservoir. Although the heat transfer medium 50 is shown as being present in the reservoir 66 as provided in FIG. 3B, it should be understood that the heat transfer medium 50 can also be provided in a series of channels, as illustrated in FIG. 3A. When present as a layer or sheet and provided as a solid or having a flexible matrix, the shape conforming medium 64 of this aspect of the present technology may be a magnetorheological elastomer (MRE, otherwise known as a magnetosensitive elastomer), or include a magnetorheological foam (MR-foam). In certain instances, MREs with a porous matrix may also be referred to as foams or having a foamed matrix. Distinguished from an MRF, the presence of the layer of shape conforming material 64 as having a solid matrix base or a flexible matrix base (as an MRE or MR-foam) may minimize or otherwise avoid potential problems, such as particle settling of the ferromagnetic particles, as discussed above. For simplicity, FIG. 3C illustrates one layer of the shape conforming material 64. It should be understood that the MRE shape conforming material 64 can be provided in multiple layers. The layers may be adjacent one another, or separated as having an inner layer, an outer layer, and the like. Still further, the MRE may be provided in strips that may be aligned with one another or spaced apart having various designs and strengths. In this regard, it is envisioned that the strips and/or layers may be provided having different materials (elastomers and/or ferromagnetic particles), leading to different rigidity and the ability to customize the clinical wrap 22. The MRE may also be presented with a weaved or shaped pattern or having various lattice structures.

MREs may include a class of elastomers that contain a polymeric matrix with embedded nano- to micro-sized ferromagnetic particles, such as carbonyl iron, arranged in a particular pattern. Common MREs may generally include a natural or synthetic rubber matrix that is then interspersed with the ferromagnetic particles. MR-foams generally provide an absorptive metal foam matrix in which a controllable fluid having the ferromagnetic particles is contained. Non-limiting exemplary metal foams may include aluminum, copper, and nickel.

Various different MREs can be prepared using a curing process. In one aspect, a liquid base polymer, such as silicone rubber, can be mixed with an iron powder, as well as other desired additives, and cured at a high temperature in the presence of a magnetic field. The presence of the magnetic field during the curing process is what causes a chain-like structural arrangement of the iron particles, which then results in an anisotropic material. Alternatively, it is envisioned that 3D printing techniques may also be used to configure the magnetic particles into a polymer matrix. The composite microstructure of an exemplary MRE is such that the mechanical properties of the material can be thereafter be accurately controlled with the application of a magnetic field. In other words, if a magnetic field is not applied during the curing process, the resulting material will be generally be considered an elastomer ferromagnet composite (EFC) that would essentially have little or no influence on the shape conforming medium 64. This is because the solid elastomer matrix of the EFC would prevent the ferromagnetic particles from forming chains, which is required for the change in apparent viscosity as described below.

Whether present as an MRF, MRE, MR-foam, or equivalent, upon selective activation of the shape conforming medium 64 using a controlled stimulus, i.e., the generation of one or more magnetic field, the ferromagnetic particles disposed therein are nearly instantaneously (within milliseconds in most occurrences) aligned into chains and/or particle clusters that are substantially parallel to the magnetic flux/field lines. Depending on the ferromagnetic materials and strength of the magnetic field that is generated, such chains may interconnect and form fibrils that may be branched from the chains. Clusters of these chains/fibrils exhibit a very high strength and, thus, increase the rigidity of the shape conforming material 64 such that the clinical wrap 22 (or at least one region thereof) is functionally immobile, and will require a large amount of force in order to bend or flex. Subsequent deactivation, or removal of the magnetic field, will no longer maintain the clusters of chains/fibrils in an aligned orientation, and the apparent viscosity of the shape conforming material 64 will substantially decrease, allowing the clinical wrap 22 to bend and flex again. It is envisioned that the activation and deactivation of the magnetic field can be repeated and performed any number of times, which permits ease of realignment and reuse of the clinical wraps 22.

During use, the clinical wrap 22 is first contoured adjacent a patient 20 in its flexible state. Once in a desired location adjacent the patient 20, a magnetic field is generated near the clinical wrap 22. The rigidity of the shape conforming medium 64 substantially increases as the ferromagnetic material in the fluid, elastomer, and/or foam is realigned, to the extent that the clinical wrap 22 is now in a rigid state, which assists in providing an immobilization of the patient or region of the patient requiring care or treatment. Deactivation or removal of the magnetic field then returns the rigidity to its original/prior state, and the clinical wrap 22 is in its more flexible state, and can be reshaped or removed.

Magnetic fields are flux forces that generally arise due to the movement of an electrical charge. The movement of electrical charge may occur via the movement of electrons in an electric current, known as electromagnetism, or via the quantum-mechanical spin and orbital motion of electrons in an atom. For example, a wire that has an electrical current running through it creates a magnetic field. Thus, in various aspects of the present technology, the clinical wrap 22 may be provided with an electrically conductive circuit 72 disposed throughout at least one region. The electrically conductive circuit 72 is configured to selectively generate the magnetic field which, in turn, increases the apparent viscosity of the shape conforming medium 64, providing the immobilizing features of the clinical wrap 22. In still other aspects, one or more magnet can be provided in the clinical wrap. In various aspects, the magnet may be an electromagnet, a permanent magnet, or a combination of both.

As shown in FIGS. 3A-3C, the electrically conductive circuit 72 may include a number of wires 74 arranged in a predetermined pattern within the clinical wrap 22. As shown, the wires 74 may be disposed between the outermost layer 36 and the channel circuits 48, 62. In other aspects, the wires 74 may be provided surrounding the sides of the channels 46 containing the shape conforming medium 64. The wires 74 should be provided at an appropriate gauge thickness such that the passage of an appropriate amount of low voltage current through the wires will provide the necessary magnetic field required to activate the immobilization features of the clinical wrap 22 to provide a desired rigidity. In certain aspects, the wires 74 are provided wound in a coil shape, or the like, in order to generate a magnetic field.

In other aspects, the magnetic field can be generated by an electromagnet or electrically conductive circuit that is separate and distinct from the clinical wrap 22. In one example, with reference to FIG. 4, a patient support apparatus 76 may be provided with the capability of generating a magnetic field configured to operate the clinical wrap 22. While the patient support apparatus 76 is generally shown as a patient bed in FIG. 4, other conventional patient support apparatuses may also be used, such as stretchers, cots, tables, benches, stationary chairs and seats, wheelchairs, and the like. In one specific aspect, a bed component, such a mattress pad 78 that defines a patient support surface of a patient support apparatus 76 may be provided with a number of different segmented areas 80 that may each contain an appropriately configured electromagnet 82 (or electrically conductive circuit) strategically disposed therein and configured to generate a suitable magnetic field to work with the clinical wrap 22.

Figure 4:
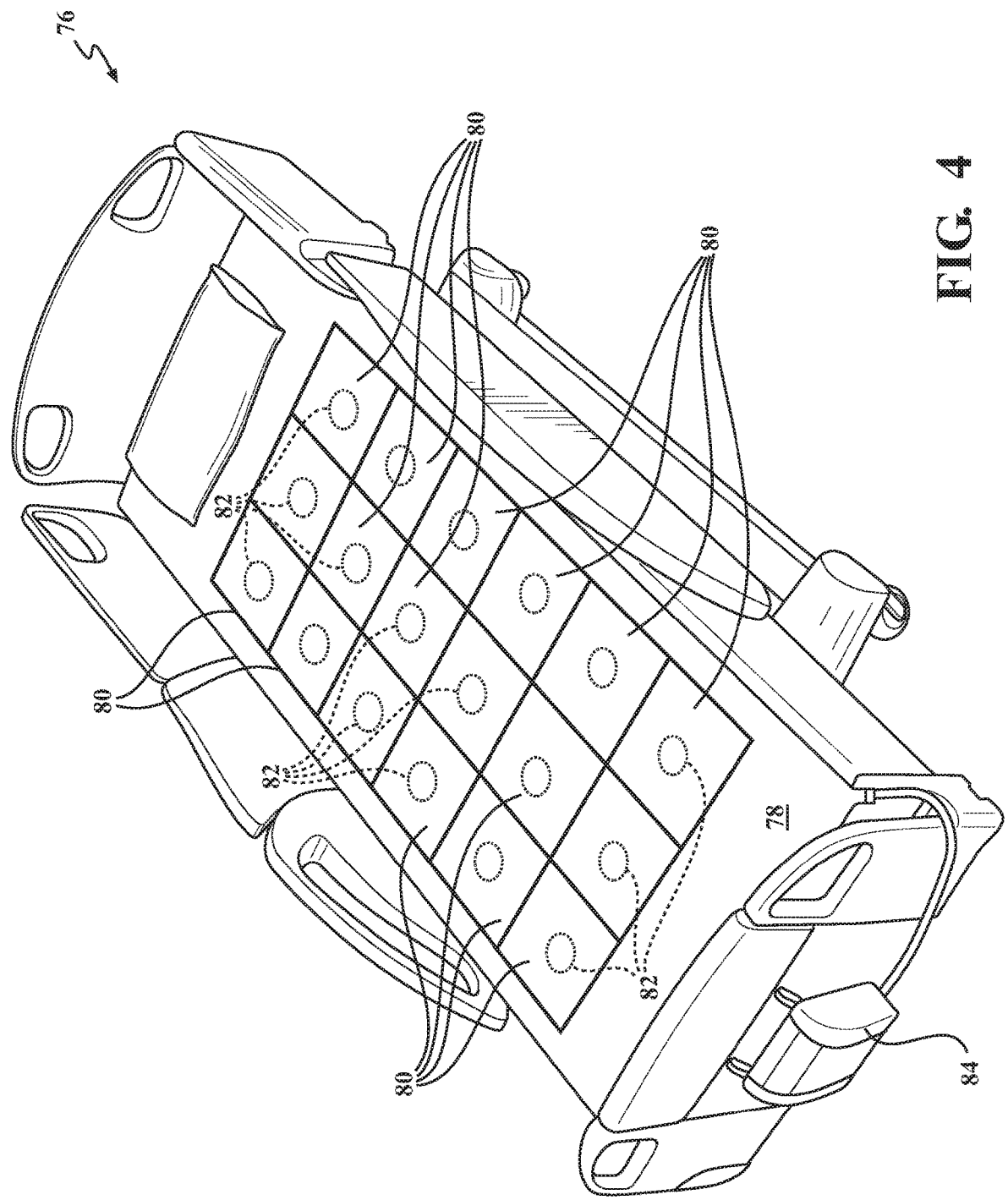
FIG. 4 is an isometric view of an exemplary patient support apparatus that may be used with the clinical wrap of the present technology.

In various aspects, one or more controller 84 (FIG. 1) may be provided to control and manage various aspects of the present technology. For example, the controller 84 may be programmed and configured to monitor and control the electrically conductive circuit 72 disposed within the clinical wrap 22, and provide the appropriate level of current through the various wires 74 resulting in a desired level of stiffness and rigidity of the clinical wrap 22. The controller 84 may also be configured to work with the heat exchanger 56, for example, to monitor and/or regulate the heating and cooling thermal management features of the present technology. In certain aspects, the controller 84 may be remotely monitored, operated, or programmed, via an appropriate wired or wireless connection, by a caregiver or medical professional. In certain aspects where the clinical wrap 22 may be used outside of a medical or care facility, the controller 84 may be provided with a portable source of power, such as a battery. In still other aspects, a battery (or other source of electrical current) may be separately provided in order to generate the appropriate magnetic fields. The patient support apparatus 76, as well as the electromagnet 82 or other source providing the magnetic field may also be managed by the controller 84. Alternatively, it is also envisioned that the controller 84 can be coupled to, or an integral part of, the patient support apparatus 76, as shown in FIG. 4.

In discussed above, the clinical wrap 22 may be provided with various zones 58, 60 that may exhibit different apparent viscosities based on having different magnetic field strengths, or be provided with different temperatures. In various aspects, the zones 58, 60 may be distinguished from one another as being different thermal zones, and/or different pressure zones. Different thermal zones can be managed by the heat exchanger 56 and/or the controller 84. In certain examples, the wires 74 of the different pressure zones may be provided with a different gauge thickness, or the wires 74 may be provided with a different amount of current passing there through, providing a magnetic field of different strengths, which may be managed by the controller 84.

In certain aspects, the shape conforming medium 64 may also be configured to be thermally conductive, which may assist with the thermal conduction/convection process.

In still other aspects, it is envisioned that the shape conforming medium 64 may include one or more ultraviolet (UV) curable resins, or phase-change material (PCM) in an appropriate fluid carrier, as an alternative to (or in certain aspects, in addition to) a magnetorheological material. FIG. 3D is a partial cross-sectional view of a portion of the clinical wrap 22 of FIG. 2 taken along the line 3-3 according to a fourth, alternative exemplary aspect of the present teachings using a UV curable resin or PCM as the layer of shape conforming material 64 without the presence of the circuit 72 of wires 74 as provided in FIGS. 3A-3C. As discussed with respect to FIG. 3C above, although the heat transfer medium 50 is shown as being present in the reservoir 66 as provided in FIG. 3B, it should be understood that the heat transfer medium 50 can also be provided in a series of channels, as illustrated in FIG. 3A.

UV curable resins or polymers are light-activated, such that the resin or polymer changes its properties when exposed to UV light. In response to exposure to a controlled amount of UV irradiation or electron beam (EB) energy, which polymerizes and cures the UV curable resin in a short time period, the shape conforming medium 64 will exhibit an abrupt change in apparent viscosity due to the hardening/solidification of the resin upon curing. For example, the shape conforming medium 64 can include one or more non-toxic UV curable resin systems, such as epoxy acrylates or acrylated polyester curing systems. A large number of acrylic-functionalized oligomers are commercially available, including polyester and epoxy resins, aliphatic and aromatic urethanes, silicones and polyethers. Various UV curable resin systems include oligomers, monomers (diluents), a photo-polymerization initiator, coinitiators (spectral sensitizer, reducing agents, etc.) and other optional additives such as stabilizers, antioxidants, plasticizers, and pigments. While mercury vapor lamps have long been considered an industry standard for curing UV resin systems, various fluorescent and LED lamps can be used for UV curing in a number of applications, and may provide the portability that would be useful with the present technology. In various aspects, the controller 84 may be used to control and direct the UV lamps.

It should be understood that in aspects where a UV curable resin is used in the shape conforming medium 64 for purposes of altering the apparent viscosity and providing immobility, that curing process is typically irreversible, thus the clinical wrap 22 may only have a one-time use. Additionally, various other design considerations for the clinical wrap 22 are relevant for enabling the proper curing of the UV-curable resin. For example, the clinical wrap 22 should be provided with a substantially transparent outermost layer 36 adjacent to the shape conforming medium 64 in order to allow for the passage of UV light to the resins. Notably, providing certain areas of the clinical wrap 22 as transparent, or opaque, may provide additional benefits. For example, transparent or opaque areas can otherwise provide for the quick and easy visibility of IV lines, EKG leads, and the like. Of course, the clinical wrap 22 can also be provided with certain areas that are free from heat transfer materials and shape conforming materials altogether, in order to provide quick access to a certain region of the body, and to provide defibrillator accessibility.

A PCM is a substance with a high heat of fusion that is generally capable of storing and selectively releasing large amounts of energy, and melts and solidifies at a predetermined temperature. Exemplary PCMs may include organic paraffin carbohydrates, C12 to C14 alkanes, or various inorganic salts. PCMs are generally suspended within a suitable viscous carrier, such as a mineral oil, silicone fluid, or a urethane. A PCM will absorb or release thermal energy in order to maintain a regulated temperature. For example, when in a solid phase, a PCM will absorb heat as the external temperature rises until the melting point of the PCM is reached. PCMs for use with the present technology may optionally be microencapsulated so that is remains substantially evenly distributed throughout the carrier, especially after repeated cooling/warming cycles.

In still other aspects, the shape conforming medium 64 may be used in combination with one or more shape-memory materials, such as a shape-memory polymer or a shape-memory alloy provided as part of the structure of the clinical wrap 22. A shape-memory polymer is a polymer that has the ability to return from a temporary deformed state to its original state when induced by a stimulus, such as a change in temperature. A shape-memory alloy is preferably a lightweight alloy that similarly has the ability to return to its original shape after being deformed, for example, a deformed shape-memory alloy returns to its pre-deformed shape when heated. Non-limiting examples of shape-memory alloys useful with the present technology include copper-aluminum-nickel, and nickel-titanium alloys.

The heat transfer medium useful with the present technology may be a fluid or a gas. Non-limiting examples of suitable heat transfer fluids include water, an aqueous liquid, an organic liquid (such as an oil), and the like that has a heat capacity suitable for transferring heat via thermal conduction/convection techniques. Non-limiting examples of suitable heat transfer gases include air, and other non-toxic gases capable of being heated or cooled in a non-toxic manner. The heat transfer medium 50 may enter the clinical wrap 22 via the fluid inlet 52 and flow through a continuous fluid passage, such as the heat transfer circuit 48, ultimately leading to the fluid outlet 54.

As the heat transfer medium 50 travels between the fluid inlet 52 and fluid outlet 54, the temperature of the heat transfer medium 50 may increase or decrease, depending upon whether the clinical wrap 22 is being used for heating or cooling purposes. The heat exchanger 56 may include a suitable heating or cooling device, as well as a fluid pump for controlling the flow of the heat transfer medium 50 through the clinical wrap 22. In various preferred aspects, the circulation of the heat transfer medium 50 through the clinical wrap 22 is activated, optionally using the controller 84, after the shape conforming medium 64 has become rigid, thus the circulation does not affect a pressure of the innermost surface 42 of the clinical wrap 22 against the patient 20. Similarly, if the circulation of the heat transfer medium 50 is stopped, preferably the pressure is not reduced, and the innermost surface 42 of the clinical wrap 22 will remain in contact with the patient 20. In various aspects, the controller 84 may monitor at least one safety feature prior to circulating the heat transfer medium 50 through the clinical wrap 22. For example, the controller 84 may monitor a pressure between the inside surface of the clinical wrap and the patient; a temperature of the heat transfer medium; and/or a temperature of the patient to ensure proper operation of the clinical wrap 22.

The foregoing description is provided for purposes of illustration and description and is in no way intended to limit the disclosure, its application, or uses. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range, including the endpoints.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

What is claimed is:

1. A reinforcing clinical wrap with integral thermal management, the clinical wrap comprising:
   a fluid inlet;
   a fluid outlet;
   a first set of channels providing a fluid circuit for a heat transfer medium to circulate between the fluid inlet and the fluid outlet;
   a second set of channels providing fluid communication through a portion of the clinical wrap configured to interface with a patient, the second set of channels being shaped to selectively maintain the clinical wrap in a configuration to immobilize at least a portion of the patient; and
   a shape conforming medium disposed in the second set of channels providing selective reinforcement support of the portion of the clinical wrap to conform to a surface of a patient, and wherein the shape conforming medium comprises a magnetorheological fluid and exhibits a variable viscosity in response to exposure to a magnetic field, the clinical wrap being configured to wrap around a body portion of a patient.

2. The clinical wrap according to claim 1, wherein the magnetorheological fluid comprises a distribution of ferromagnetic particles with a range of densities to minimize particle settling and agglomeration.

3. The clinical wrap according to claim 1, further comprising an electrically conductive circuit disposed throughout the clinical wrap and configured to selectively generate a magnetic field.

4. The clinical wrap according to claim 1, wherein the fluid circuit is configured to circulate a heat transfer medium selected from the group consisting of air and water.

5. The clinical wrap according to claim 1, wherein the first and second sets of channels are arranged in an alternating side-by-side alignment with one another.

6. The clinical wrap according to claim 1, wherein the first set of channels defines at least two thermal zones configured for selectively maintaining different temperatures.

7. The clinical wrap according to claim 1, wherein the second set of channels defines at least two pressure zones configured for selectively maintaining different pressures.

8. The clinical wrap according to claim 1, further comprising at least one pressure sensor configured to detect a pressure at an interface between the clinical wrap and the patient.

9. A system for stabilizing a patient with a reinforcing clinical wrap having integral thermal management, the system comprising:
   a clinical wrap comprising:
      a fluid circuit for circulating a heat transfer medium between a fluid inlet and a fluid outlet;
      a set of channels providing fluid communication through a portion of the clinical wrap configured to interface with the patient, the set of channels being shaped to selectively maintain the clinical wrap in a configuration to immobilize at least a portion of the patient; and
      a shape conforming medium disposed in the set of channels configured to provide selective reinforcement support of the portion of the clinical wrap to conform to a surface of a patient when a magnetic field is generated,
      the clinical wrap being configured to wrap around a body portion of a patient;
   a heat exchanger configured to maintain a predetermined temperature of the heat transfer medium; and
   a controller configured to selectively activate a generation of the magnetic field.

10. The system according to claim 9, wherein the shape conforming medium comprises a magnetorheological fluid and exhibits a variable viscosity in response to exposure to the magnetic field.

11. The system according to claim 9, wherein the clinical wrap further comprises an electrically conductive circuit disposed throughout the clinical wrap and configured to selectively generate the magnetic field.

12. The system according to claim 9, wherein the set of channels is shaped to selectively maintain the clinical wrap at a predetermined configuration to immobilize at least a portion of the patient.

13. The system according to claim 9, further comprising an electromagnet selectively activated by the controller and configured to generate the magnetic field, wherein the electromagnet is disposed adjacent a patient support surface of a patient support apparatus.

* * * * *